United States Patent [19]

Tachibana

[11] Patent Number: 5,514,818
[45] Date of Patent: May 7, 1996

[54] RESOLUTION OF STEREOISOMERS OF ALIPHATIC EPOXIDES

[75] Inventor: Kozo Tachibana, West Chester, Pa.

[73] Assignee: Daicel Chemical Industries, Ltd., Sakai, Japan

[21] Appl. No.: 386,865

[22] Filed: Feb. 10, 1995

Related U.S. Application Data

[63] Continuation-in-part of Ser. No. 122,288, Sep. 17, 1993, abandoned.

[51] Int. Cl.$^6$ ............ C07D 301/32; C07D 303/04; C07D 303/08; C07D 303/14
[52] U.S. Cl. ............ 549/541; 549/542; 549/555; 549/557; 549/561; 549/563
[58] Field of Search ............ 549/541, 542

[56] References Cited

U.S. PATENT DOCUMENTS

| | | | |
|---|---|---|---|
| 2,292,293 | 8/1942 | Rose | 568/863 |
| 2,518,235 | 8/1950 | Hartstra et al. | 568/863 |
| 2,917,390 | 12/1959 | Apel et al. | 568/863 |
| 4,683,341 | 7/1987 | Ishii et al. | 568/366 |
| 5,296,618 | 3/1994 | Aaltonen et al. | 49/541 |

FOREIGN PATENT DOCUMENTS

| | | |
|---|---|---|
| 0121776 | 10/1984 | European Pat. Off. . |
| 0158884 | 10/1985 | European Pat. Off. . |
| 0157365 | 10/1985 | European Pat. Off. . |
| 0156382 | 10/1985 | European Pat. Off. ............ 549/541 |
| 0436722 | 7/1991 | European Pat. Off. . |
| 0569992 | 11/1993 | European Pat. Off. . |

OTHER PUBLICATIONS

Armstrong et al., *Anal. Chem.*, vol. 62, pp. 914–923 (1990).
Oliw, E. H., *Journal of Chromatography*, vol. 583, pp. 231–235 (1992).
Hammonds et al., *Analytical Biochemistry*, vol. 182, No. 2, pp. 300–303 (1989).
Hammonds et al., *Chemical Abstracts*, vol. 112, No. 1, Abstract No. 775n (1990).

*Primary Examiner*—Joseph E. Evans
*Attorney, Agent, or Firm*—Birch, Stewart, Kolasch & Birch

[57] ABSTRACT

A method of resolving a mixture of stereoisomers of an aliphatic epoxide containing two or less oxygen atoms is provided. The method comprises utilizing a polysaccharide or a derivative thereof as a resolving agent.

20 Claims, No Drawings

RESOLUTION OF STEREOISOMERS OF ALIPHATIC EPOXIDES

The present application is a Continuation-in-Part of co-pending U.S. Patent application Ser. No. 8/122,288 filed on Sep. 17, 1993, now abandoned, which is incorporated herein by reference in its entirety.

FIELD OF THE INVENTION

The present invention relates to a method of resolving stereoisomers of aliphatic epoxides, and especially to the resolution of enantiomeric isomers thereof.

BACKGROUND OF THE INVENTION

Since one enantiomer of an asymmetric compound can differ from another enantiomer of that asymmetric compound in its actions within a living body, methods capable of providing optical resolution of enantiomeric mixtures as well as asymmetric synthesis methods have been considered important in organic chemistry.

Generally, compounds represented by Formula (1) set forth hereinbelow, are highly reactive and at the same time possess a unique chemical reactivity, because of strain associated with the three-membered ether ring. Various chemical conversions of the Formula (1) compounds are possible through ring opening reactions, and therefore, these compounds are important intermediates in the synthesis of organic compounds, and are also important as monomers in forming epoxy resins.

Stereoisomers of aliphatic epoxides can be used as raw materials in the synthesis of various compounds. Accordingly, if they could be analyzed, and also produced through a process that could be easily carried out on an industrial scale, a great contribution to the chemical arts would be made.

As conventional processes for obtaining optically active compounds, there are asymmetric synthesis methods, optical resolution methods by way of a diastereomer, and biochemical synthesis methods using an enzyme of a microorganism. Asymmetric synthesis processes have a drawback in that an intended compound having a high optical purity usually cannot be obtained. Similarly, processes which proceed by way of a diastereomer are difficult and equimolar amounts of different optically active compounds are necessary. Furthermore, biochemical synthesis processes are inadequate in that it is often quite difficult to find an appropriate enzyme or microorganism capable of achieving a desired synthesis.

A chiral separation of an aliphatic epoxide using a derivatized cyclodextrin as a chiral stationary phase (CSP) for a capillary gas chromatography column was reported by Professor Armstrong in *Anal. Chem.*, 1990, Volume 62, pp. 914–923 and in *A Guide to Using Cyclodextrin Bonded Phases for Gas Chromatography*, (1990 Edition), Astec Co. However, these methods did not provide a good separation that could be used for a trace analysis of one of the enantiomers. In addition, gas chromatography methods are only suitable for analytical purposes, instead of being applicable to the preparation of stereoisomers.

On the contrary, liquid and supercritical fluid based chromatography methods can be used for both analytical purposes and the preparation of stereoisomers. There were a few separations of esters of epoxy higher fatty acids reported in the *Journal of Chromatography, Biomedical Applications*, Vol. 583, No. 2, pp. 231–235 (1992), and *Anal. Biochem.*, Vol. 182, No. 2, pp. 300–303 (1989). However, of known liquid (and supercritical fluid) chromatographic CSPs, no one has previously reported to be able to separate stereoisomers of an aliphatic epoxide which has two or less attractive interaction points for hydrogen bonding, because such stereoisomers, whose difference is only based on the three dimensional structural difference, were heretofore believed to possess too little functionality to be enanitiomerically separated. In contrast, it is easy to recognize chirality if there exists three or more attractive interaction points for hydrogen bonding-like in the epoxy esters or epoxy acids illustrated immediately below. In this regard, three attractive interaction points (i.e., oxygen atoms) are available in such esters and acids for an attractive interaction, e.g., with a chiral stationary phase.

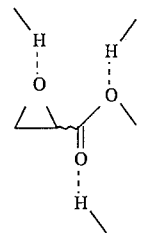

In the above illustrated epoxy esters and acids, the "dotted lines", indicate the presence of hydrogen bonding between oxygen atoms in the epoxy esters and acids and other molecules (e.g., in a chiral stationary phase).

SUMMARY OF THE INVENTION

The invention provides a method for the resolution of a mixture of stereoisomers of an aliphatic epoxide having the below shown Formula (1) structure. The method utilizes a resolving agent to perform the resolution, with the resolving agent comprising a polysaccharide or a derivative thereof.

The aliphatic epoxides of Formula (1) are as follows:

(1)

in which $R_1$, $R_2$, $R_3$ and $R_4$ are the same or different and are selected from the group consisting of:

hydrogen, and a substituted or unsubstituted, saturated or unsaturated aliphatic group having 1 to 30 carbon atoms (exclusive of substituents), which aliphatic group when substituted contains one or more substituents selected from the group consisting of a hydroxyl moiety, a halogenated moiety, an ether moiety, and like moieties; provided that the total number of oxygen atoms in the Formula (1) epoxide is two or less.

DETAILED DESCRIPTION OF THE INVENTION

The following Detailed Description, including the examples reported herein, is provided as an aid to those desiring to practice the present invention and is not to be construed as limiting to the scope of the inventor's discovery. In this respect the present invention is only to be limited by the scope of the claims appended hereto and the equivalents thereof.

In Formula (1), the substituents $R_1$ to $R_4$ can generally be the same or different and are selected from the group consisting of (1) hydrogen and (2) substituted or unsubstituted, saturated or unsaturated, aliphatic groups having 1 to 30 carbon atoms (exclusive of substituents), with acceptable saturated aliphatic groups including $C_{1-30}$ alkyl moieties, and acceptable unsaturated moieties including $C_{1-30}$ alkenylic moieties (having up to 5 double bonds) and $C_{1-30}$ alkynylic moieties (having up to 5 triple bonds), and mixtures thereof; provided that the total number of oxygen atoms in the Formula (1) epoxide is two or less.

As specific examples of the $R_1$ to $R_4$ substituents that are present on the aliphatic epoxides of Formula (1) shown above there are mentioned —H, —$CH_3$, —$CH_2CH_3$, $(CH_2)_nCH=CH_2$ (n=0-4), —$CH_2OH$, —$CH_2$—F, —$CH_2$—Cl, —$CH_2$—Br, —$OCH_3$, —$(CH_2)_nCH_3$ (n=3-25), —$(CH_2)_4CH(CH_3)_2$, and the like.

The resolving agent used in the present invention comprises a polysaccharide or a derivative thereof, in an effective amount to effect a resolution of a mixture of stereoisomers encompassed by Formula (1). When the stereoisomers of Formula I which are being resolved are optically active compounds, the polysaccharide or derivative thereof is preferably optically active. Synthetic polysaccharides, natural polysaccharides and modified natural polysaccharides may be used in the inventive methods. Homoglycans having a high regularity are preferred and it is preferred that the bonding mode thereof be constant. Furthermore, it is preferred that a polysaccharide having a high purity be utilized which can be easily obtained. As preferred examples of a polysaccharide useful in the present invention, there are mentioned cellulose, amylose, β-1,4-chitosan, chitin, β-1,4-mannan, β-1,4-xylan, inulin, α-1,3-glucan, and β-1,3-glucan. When the chosen resolving agent is a polysaccharide derivative, a part or all, preferably at least 85%, of hydrogen atoms on hydroxyl groups of the polysaccharide (like one of the foregoing), are preferably replaced by other atomic groups such as:

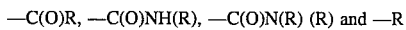

—C(O)R, —C(O)NH(R), —C(O)N(R) (R) and —R wherein R stands for an aliphatic group having 1 to 3 carbon atoms, an alicyclic group having 3 to 8 carbon atoms or an aromatic or heteroaromatic group having 4 to 20 carbon atoms, any of which R groups may optionally be substituted with a substituent.

The above-described types of polysaccharides and polysaccharide derivatives can be easily obtained by various known reactions. Moreover, these polysaccharides and their derivatives are especially suitable for chromatographic separation carried out on an industrial scale because they are easily available as starting materials and their stability is high.

Accordingly, in the chromatographic processes of the present invention, if an appropriate resolving agent is selected from the polysaccharides and derivatives thereof defined above, the stereoisomers of an aliphatic epoxide of Formula (1) can be resolved.

When liquid or supercritical fluid chromatography is adopted as a means for carrying out the method of the present invention, the chosen polysaccharide or its derivative is packed in a column directly or after it has been supported on a suitable carrier.

Since a granular resolving agent is preferred for liquid and supercritical chromatographic separation, when the polysaccharide or its derivative is used as the resolving agent, it is preferred that the polysaccharide or its derivative be pulverized or formed into beads. The particle size is variable according to the size of the column or plate used, but it is ordinarily 1 μm to 10 mm and preferable 1 μm to 300 μm. It is also preferred that the particles be porous.

In order to improve the pressure resistance of the resolving agent, prevent swelling or shrinkage by the solvent substitution and increase the number of theoretical stages, it is preferred that the polysaccharide or its derivative be supported on a carrier. The size of the carrier is variable according to the size of the column or plate used, but it is ordinarily 1 μm to 10 mm and preferably 1 μm to 300 μm. It is preferred that the carrier be porous, and the average pore size is 10 Å to 100 μm, preferably to 50 Å to 10,000 Å. The amount of the polysaccharide or its derivative held on the carrier is ordinarily 1 to 1200% by weight and preferably 5 to 50% by weight based on the carrier.

Either a chemical method or a physical method may be used to support a polysaccharide or a derivative thereof on a carrier. As a physical method, there is mentioned (1) a method in which a polysaccharide or its derivative is dissolved in a solvent to form a solution, the solution is sufficiently mixed with a carrier and the solvent is distilled off under reduced pressure or by heating or by an air current, and (2) a method in which a polysaccharide or its derivative is dissolved in a solvent to form a solution, the solution is sufficiently mixed with a carrier and the mixture is stirred and then disbursed in a liquid having no compatibility with the solvent so as to diffuse the solvent. A heat treatment or the like may be performed so as to crystallize the polysaccharide or its derivative on the carrier. Moreover, there may be adopted a method in which a small amount of a solvent is added to swell or dissolve the polysaccharide or its derivative and the solvent is then distilled off to change the supported state and the resolving characteristics of the polysaccharide or its derivative.

A porous organic carrier and a porous inorganic carrier can be used, and a porous inorganic carrier is preferable. As preferred examples of the porous organic carrier, there are polymeric substances such as polystyrene, polyacrylamide and polyacrylate, and as preferred examples of the porous inorganic carrier, there are synthetic and natural substances such as silica, alumina, magnesia, titanium oxide, glass, silicate and kaolin. A surface treatment may be carried out so as to improve the carrier's affinity with the polysaccharide or its derivative. As the surface treatment, there are mentioned silane treatments using an organic silane compound and plasma polymerization surface treatments.

When a polysaccharide or its derivative is used for the resolution, even in chemically identical derivatives, resolution characteristics can differ according to physical properties such as the molecular weight, the degree of crystallization and the orientation. Accordingly, the polysaccharide or its derivative may be subjected to a physical or chemical treatment such as a heat treatment or an etching treatment after giving a shape to the carrier suitable for the intended use, or during the step of giving a shape to the carrier suitable for the intended use.

In the case where thin layer chromatography is carried out when practicing the present inventive methods, a layer having a thickness of 0.1 to 100 mm, which is composed of particles of the resolving agent of the present invention having a size of about 0.1 μm to about 0.1 mm and, optionally, a small amount of a binder, may be formed on a supporting plate.

As means for obtaining a pure isomer by using the above-mentioned resolving agent in the present invention, there are mentioned chromatographical processes such as liquid chromatography, a simulated moving bed adsorption system, supercritical fluid chromatography and thin layer chromatography. Gas chromatography is not a suitable means for obtaining a pure isomer utilizing the present inventive methods.

When practicing the present inventive methods and when liquid chromatography, supercritical fluid chromatography and thin layer chromatography are utilized, typical solvents may be used in addition to a solvent for the polysaccharide or the derivative thereof. If the resolving agent is chemically bonded to the carrier or is insolubilized by crosslinking, any liquids other than reactive liquids may be used without any limitations. Of course, the resolution characteristics of a compound or an optical isomer vary according to the kind of the developing solvent, so that it is generally thought preferable and desirable to examine various solvents.

Utilizing the present invention, a stereoisomer of a compound represented by the general formula (1) which is an important industrial material, can be easily analyzed and obtained in a purified form, while using a cheap starting material and adopting a simple chemical conversion and a chromatographic technique. Accordingly, the inventive resolution methods make great contributions to the synthesis of many useful achiral and chiral compounds. That is, the invention provides a useful method of analyzing as well as producing stereoisomers of the aliphatic epoxides of Formula (1) shown above.

The present invention will now be described in detail with reference to the following examples that by no means limit the scope of the invention.

The liquid chromatography column utilized in the following Examples was a stainless column having a length of 25 cm and an inner diameter of 0.46 cm. It was packed with a filler which comprised silica gel treated with diphenylsilane and about 20 weight % of cellulose tris(3,5-dimethylphenylcarbamate) supported on the silica gel of 5 μm (CHIRALCEL®OD-H). It was also packed with fillers which comprised silica gel treated with aminopropylsilane followed by 3,5-dimethylphenyl isocyanate and 20 weight % of amylose tris(3,5-dimethylphenylcarbamate) (CHIRALPAK®AD) or amylose tris((S)-methylbenzylcarbamate) (CHIRALPAK®AS) supported on the silica gel of 10 μm (CHIRALCEL® and CHIRALPAK® are registered trademarks of Daicel Chemical Industries, Ltd.).

The stereoisomer eluted out was detected with a refractive index detector, ERMA ERC-7515A, a tradename of Erma CR.INC., an optical rotatory detector, SHODEX OR-1, a tradename of Showa Denko. A 880-PU, a tradename of Jasco was used as a liquid chromatography device with an injector, RHEODYNE 7125, a tradename of Rheodyne, and a degasser, ERC-3611, a tradename of Erma CR.INC.

The definitions of the terms used in the examples are as follows:

$$\text{Capacity factor } (k_n') = \frac{(\text{retention volume of peak number } n) - (\text{dead volume})}{(\text{dead volume})}$$

$$\text{Separation Factor } (\alpha) = \frac{(\text{capacity factor of more strongly retained isomer})}{(\text{capacity factor of less strongly retained isomer})}$$

$$\text{Resolution factor } (Rs) \; (n > m) = \frac{(\text{retention vol. of peak no. } n) - (\text{retention vol. of peak no. } m)}{(\text{sum of band widths of both peaks})/2}$$

TABLE 1

EXAMPLE 1
Separation on CHIRALCEL® OD-H

| $R_1$ | $R_2$ | $R_3$ | $R_4$ | Eluent | $k_1'$ | Elution Order (faster/later) | α | Rs |
|---|---|---|---|---|---|---|---|---|
| —H | —H | —H | —CH$_2$CH$_3$ | A | 0.53 | +/− | >1.00* | — |
| —H | —H | —H | —CH$_2$OH | A | 1.73 | +/− | >1.00* | — |
| —H | —H | —H | —CH$_2$F | A | 1.01 | −/+ | >1.00* | — |
| —H | —H | —H | —CH$_2$Cl | A | 0.96 | −/+ | >1.00* | — |
| —H | —H | —H | —CH$_2$Br | A | 0.99 | −/+ | >1.00* | — |
| —H | —H | —H | —CH$_3$ | A | 0.58 | +/− | >1.00* | — |
| —H | —CH$_3$ | —H | —CH$_3$ | A | 0.5 | +/− | >1.00* | — |
| —H | —H | —H | —(CH$_2$)$_7$CH$_3$ | A | 0.41 | −/+ | >1.00* | — |
| —H | —H | —H | —(CH$_2$)$_9$CH$_3$ | A | 0.38 | −/+ | >1.00* | — |
| —(CH$_2$)$_9$CH$_3$ | —H | —H | —(CH$_2$)$_4$CH(CH$_3$)$_2$ | A | 0.28 | −/+ | >1.00* | — |
| —H | —H | —H | —(CH$_2$)$_{11}$CH$_3$ | A | 0.36 | −/+ | >1.00* | — |
| —H | —H | —H | —(CH$_2$)$_{13}$CH$_3$ | A | 0.34 | −/+ | >1.00* | — |
| —H | —H | —H | —(CH$_2$)$_{15}$CH$_3$ | A† | 0.32 | −/+ | >1.00* | — |
| —CH$_3$ | —CH$_3$ | —H | —OCH$_3$ | A | 0.54 | +/− | 1.12 | 1.31 |

Condition A:
Flow Rate: 1.0 ml/min
Temperature: Ambient
Volume of Injection: 0.2 μl (neat)
Hexane/2-Propanol = 95/5
*: Though α-value was not large enough to get a splitting peak by the refractive index detector, there was a clear indication of chiral separation by the optical rotatory detector.
†: 2 μl of 100 mg/ml sample was injected.

TABLE 2

EXAMPLE 2
Separation on CHIRALPAK ® AD

| $R_1$ | $R_2$ | $R_3$ | $R_4$ | Eluent | $k_1'$ | Elution Order (faster/later) | α | Rs |
|---|---|---|---|---|---|---|---|---|
| —H | —H | —H | —$CH_2CH_3$ | B | 0.64 | +/− | 1.10 | 1.23 |
| —H | —H | —H | —$CH_2OH$ | B | 4.17 | −/+ | 1.26 | 4.13 |
| —H | —H | —H | —$CH_2F$ | B | 1.43 | −/+ | 1.10 | 1.78 |
| —H | —H | —H | —$CH_2Cl$ | B | 2.50 | −/+ | 1.42 | 4.06 |
| —H | —H | —H | —$CH_2Br$ | B | 3.66 | −/+ | 1.49 | 3.36 |
| —H | —H | —H | —$CH_3$ | A | 0.60 | +/− | 1.04 | — |
| —H | —H | —H | —$CH=CH_2$ | A | 0.62 | −/+ | >1.00* | — |
| —$CH_3$ | —H | —H | —$CH_3$ | A | 0.65 | trans/cis** | 1.18** | 1.75** |
| —H | —$CH_3$ | —H | —$CH_3$ | A | 0.55 | −/+ | >1.00* | — |
| —H | —H | —H | —$(CH_2)_3CH_3$ | A | 0.46 | −/+ | >1.00* | — |
| —H | —H | —H | —$(CH_2)_7CH_3$ | A | 0.33 | −/+ | >1.00* | — |
| —H | —H | —H | —$(CH_2)_9CH_3$ | A | 0.29 | −/+ | >1.00* | — |
| —$(CH_2)_9CH_3$ | —H | —H | —$(CH_2)_4CH(CH_3)_2$ | A | 0.23 | −/+ | >1.00* | — |
| —H | —H | —H | —$(CH_2)_{11}CH_3$ | A | 0.27 | −/+ | >1.00* | — |
| —H | —H | —H | —$(CH_2)_{13}CH_3$ | A | 0.25 | −/+ | >1.00* | — |
| —H | —H | —H | —$(CH_2)_{15}CH_3$ | A† | 0.22 | −/+ | >1.00* | — |
| —$CH_3$ | —$CH_3$ | —H | —$OCH_3$ | A | 0.55 | −/+ | >1.00* | — |

Condition A:
Flow Rate: 1.0 ml/min
Temperature: Ambient
Volume of Injection: 0.2 μl (neat)
Hexane/2-Propanol = 95/5
Condition B:
Flow Rate: 1.0 ml/min
Temperature: Ambient
Volume of Injection: 0.2 μl (neat)
Hexane/Ethanol = 90/10
*: Though α-value was not large enough to get a splitting peak by the refractive index detector, there was a clear indication of chiral separation by the optical rotatory detector.
**: An achiral compound. It may be separated from its trans-isomer. Values relate to its transform.
†: 2 μl of 100 mg/ml sample was injected.

TABLE 3

EXAMPLE 3
Separation on CHIRALPAK ® AS

| $R_1$ | $R_2$ | $R_3$ | $R_4$ | Eluent | $k_1'$ | Elution Order (faster/later) | α | Rs |
|---|---|---|---|---|---|---|---|---|
| —H | —H | —H | —$CH_2CH_3$ | A | 0.62 | +/− | 1.14 | — |
| —H | —H | —H | —$CH_2OH$ | B | 2.01 | +/− | 1.04 | — |
| —H | —H | —H | —$CH_2F$ | A | 1.50 | −/+ | 1.11 | 1.19 |
| —H | —H | —H | —$CH_2Cl$ | A | 1.38 | −/+ | 1.15 | 1.56 |
| —H | —H | —H | —$CH_2Br$ | A | 1.41 | −/+ | 1.15 | 1.64 |
| —H | —H | —H | —$CH_3$ | A | 0.67 | +/− | 1.18 | 1.44 |
| —H | —H | —H | —$CH=CH_2$ | C | 1.20 | −/+ | 1.17 | 0.67 |
| —$CH_3$ | —H | —H | —$CH_3$ | A | 0.54** | trans/cis** | 1.22** | 1.65** |
|  |  |  |  |  | 0.66** | cis/trans** | 1.30** | 1.94** |
| H | —$CH_3$ | —H | —$CH_3$ | A | 0.54 | +/− | 1.58 | 3.47 |
| —H | —H | —H | —$(CH_2)_3CH_3$ | A | 0.53 | +/− | 1.25 | 1.94 |
| —H | —H | —H | —$(CH_2)_7CH_3$ | C | 0.50 | +/− | 1.26 | 1.68 |
| —H | —H | —H | —$(CH_2)_9CH_3$ | D | 0.40 | +/− | 1.24 | 1.28 |
| —H | —H | —H | —$(CH_2)_2CH=CH_2$ | A | 0.71 | +/− | 1.26 | 2.15 |
| —$(CH_2)_9CH_3$ | —H | —H | —$(CH_2)_4CH(CH_3)_2$ | A | 0.23 | −/+ | >1.00* | — |
| —H | —H | —H | —$(CH_2)_{11}CH_3$ | D | 0.36 | +/− | 1.22 | 1.40 |
| —H | —H | —H | —$(CH_2)_{13}CH_3$ | D | 0.32 | −/+ | 1.20 | — |
| —H | —H | —H | —$(CH_2)_{15}CH_3$ | A† | 0.27 | −/+ | 1.15 | — |
| —$CH_3$ | —$CH_3$ | —H | —$OCH_3$ | A | 0.52 | +/− | 1.07 | — |

Condition A:
Flow Rate: 1.0 ml/min
Temperature: Ambient
Volume of Injection: 0.2 μl (neat)
Hexane/2-Propanol = 95/5
Condition B:
Flow Rate: 1.0 ml/min
Temperature: Ambient
Volume of Injection: 0.2 μl (neat)
Hexane/Ethanol = 90/10
Condition C:

TABLE 3-continued

EXAMPLE 3
Separation on CHIRALPAK ® AS

| $R_1$ | $R_2$ | $R_3$ | $R_4$ | Eluent | $k_1'$ | Elution Order (faster/later) | α | Rs |
|---|---|---|---|---|---|---|---|---|

Flow Rate: 1.0 ml/min
Temperature: −10° C.
Volume of Injection: 0.2 μl (neat)
Hexane/2-Propanol = 95/5.
Condition D:
Flow Rate: 1.0 ml/min
Temperature: Ambient
Volume of Injection: 0.2 μl (neat)
Hexane/2-Propanol = 99/1
*: Though α-value was not large enough to get a splitting peak by the refractive index detector, there was a clear indication of chiral separation by the optical rotatory detector.
**: An achiral compound. It may be separated from its trans-isomer. Values relate to its trans-form.
†: 2 μl of 100 mg/ml sample was injected.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein above are expressly incorporated herein by reference in their entirety.

What is claimed is:

1. A chromatographic method for resolving a mixture of stereoisomers of an aliphatic epoxide of Formula (1), the method comprising the steps of:

under chromatographic separating conditions, other than gas chromatographic separation conditions, passing said mixture with an eluent therefor into contact with an effective amount of a resolving agent comprising a polysaccharide or a derivative thereof for performing the resolution, wherein the polysaccharide derivative is a derivative of a polysaccharide wherein at least a part of the hydrogen atoms on hydroxyl groups of the polysaccharide are replaced by a substituent selected from the group consisting of:

—C(O)R, —C(O)NH(R), —C(O)N(R) (R) and —R, wherein R stands for an aliphatic group having 1 to 3 carbon atoms, an alicyclic group having 3 to 8 carbon atoms or an aromatic or heteroaromatic group having 4 to 20 carbon atoms, any of which R groups may be optionally substituted with a substituent;

wherein the Formula (1) aliphatic epoxide is as follows:

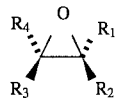

in which $R_1$, $R_2$, $R_3$ and $R_4$ are the same or different and are hydrogen, or a saturated or an unsaturated aliphatic group having 1 to 30 carbon atoms, which may be optionally substituted by one or more substituents;

provided that the total number of oxygen atoms in said Formula (1) epoxide is two or less.

2. The method of claim 1, wherein the saturated or unsaturated aliphatic group is optionally substituted by one or more substituents selected from the group consisting of:

a hydroxyl moiety, a halogenated moiety, and an ether moiety.

3. The method of claim 1, wherein the polysaccharide or the derivative thereof is optically active.

4. The method of claim 2, wherein the polysaccharide or the derivative thereof is optically active.

5. The method of claim 1, wherein the Formula (1) compound, $R_1$ to $R_4$ are the same or different and are selected from the group consisting of:

—H, —CH$_3$, —CH$_2$CH$_3$, —(CH$_2$)$_n$CH=CH$_2$ (n=0–4), —CH$_2$OH, —CH$_2$— F, —CH$_2$—Cl, —CH$_2$—Br, —OCH$_3$, —(CH$_2$)$_n$CH$_3$ (n=3–25) , and —(CH$_2$)$_4$—CH(CH$_3$)$_2$.

6. The method of claim 3, wherein the Formula (1) compound, $R_1$ to $R_4$ are the same or different and are selected from the group consisting of:

—H, —CH$_3$, —CH$_2$CH$_3$, —(CH$_2$)$_n$CH=CH$_2$ (n=0–4), —CH$_2$OH, —CH$_2$— F, —CH$_2$—Cl, —CH$_2$—Br, —OCH$_3$, —(CH$_2$)$_n$CH$_3$ (n=3–25), and —(CH$_2$)$_4$—CH(CH$_3$)$_2$.

7. The method of claim 4, wherein the Formula (1) compound, $R_1$ to $R_4$ are the same or different and are selected from the group consisting of :

—H, —CH$_3$, —CH$_2$CH$_3$, —(CH$_2$)$_n$CH=CH$_2$ (n=0–4), —CH$_2$OH, —CH$_2$ F, —CH$_2$—Cl, —CH$_2$—Br, —OCH$_3$, —CH$_2$)$_n$CH$_3$ (n=3–25), and —(CH$_2$)$_4$—CH(CH$_3$)$_2$.

8. The method of claim 1, wherein $R_1$, $R_2$ and $R_3$ are each hydrogen and $R_4$ is —CH$_2$OH.

9. The method of claim 1, wherein $R_1$, $R_2$ and $R_3$ are each hydrogen and $R_4$ is —CH$_2$F.

10. The method of claim 1, wherein $R_1$, $R_2$ and $R_3$ are each hydrogen and $R_4$ is —CH$_2$Cl.

11. The method of claim 1, wherein $R_1$, $R_2$ and $R_3$ are each hydrogen and $R_4$ is —CH$_2$Br.

12. The method of claim 1, wherein $R_1$, $R_2$ and $R_3$ are each hydrogen and $R_4$ is —CH$_2$CH$_3$.

13. The method of claim 1, wherein the polysaccharide or derivative thereof is a homoglycan having a high regularity.

14. The method of claim 1, wherein the polysaccharide is selected from the group consisting of:

cellulose, amylose, β-1,4-chitosan, chitin, β-1,4-mannan, β-1,4-xylan, inulin, α-1,3-glucan, and β-1,3-glucan.

15. The method of claim 1, wherein the polysaccharide derivative is a derivative of a polysaccharide wherein at least 85% of the hydrogen atoms on hydroxyl groups of the polysaccharide are replaced by a substituent selected from the group consisting of:

—C(O)R, —C(O)NH(R), —C(O)N(R) (R) and —R, wherein R stands for an aliphatic group having 1 to 3 carbon atoms, an alicyclic group having 3 to 8 carbon atoms or an aromatic or heteroaromatic group having 4 to 20 carbon atoms, any of which R groups may be optionally substituted with a substituent.

16. The method of claim 1, wherein said resolving agent is cellulose tris(3,5-dimethylphenylcarbamate) supported on silica gel.

17. The method of claim 1, wherein said resolving agent is amylose tris ((S)-methylbenzylcarbamate) supported on silica gel.

18. The method of claim 1, wherein said resolving agent is amylose tris (3,5-dimethylphenylcarbamate) supported on silica gel.

19. The method of claim 1, wherein said chromatographic method is a simulated moving bed adsorption system.

20. The method of claim 1, wherein said chromatographic method is a supercritical fluid chromatography method.

* * * * *